Figure 1:
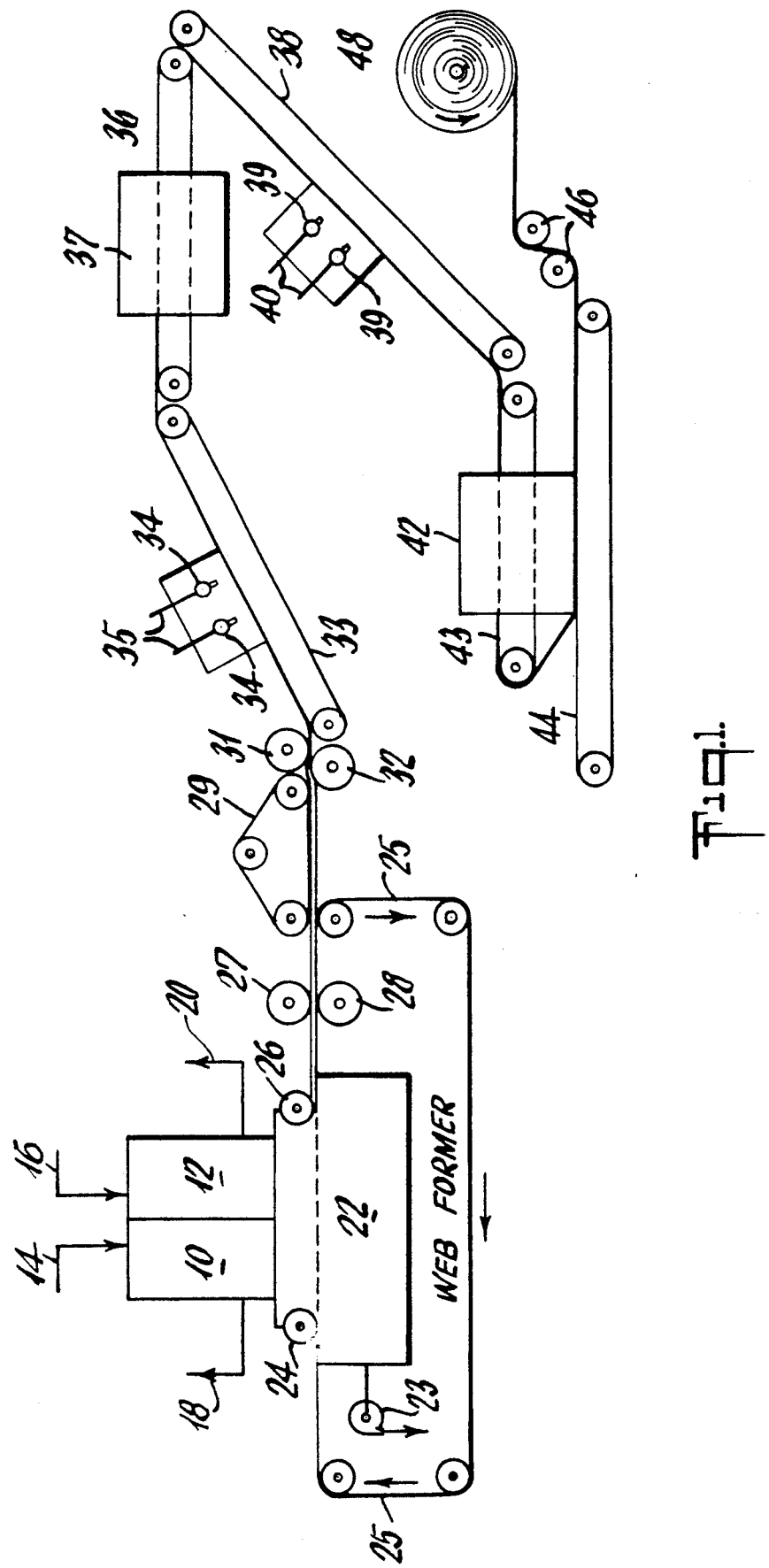

United States Patent [19]

Manning et al.

[11] Patent Number: 5,071,681
[45] Date of Patent: Dec. 10, 1991

[54] WATER ABSORBENT FIBER WEB

[75] Inventors: James H. Manning, Appleton; Kambiz B. Makoui, Menasha; David H. Hollenberg, Neenah, all of Wis.

[73] Assignee: James River Corporation of Virginia, Richmond, Va.

[21] Appl. No.: 569,216

[22] Filed: Aug. 16, 1990

Related U.S. Application Data

[62] Division of Ser. No. 225,294, Jul. 28, 1988, abandoned.

[51] Int. Cl.⁵ .............................................. B05D 3/02
[52] U.S. Cl. .................................... 427/392; 427/393; 428/290; 604/374; 604/375
[58] Field of Search ................ 427/389.9, 392, 393; 428/290, 378; 604/375, 378, 368, 374

[56] References Cited

U.S. PATENT DOCUMENTS

| | | | |
|---|---|---|---|
| 4,146,417 | 3/1979 | Drelich et al. | 428/290 |
| 4,310,593 | 1/1982 | Gross | 428/290 |
| 4,324,832 | 4/1982 | Moroff et al. | 428/290 |
| 4,340,057 | 7/1982 | Bloch et al. | 428/290 |
| 4,354,487 | 10/1982 | Oczkowski et al. | 428/290 |
| 4,413,995 | 11/1983 | Korpman | 428/289 |
| 4,443,492 | 4/1984 | Roller | 428/290 |
| 4,605,401 | 8/1986 | Chemelir et al. | 428/290 |
| 4,699,619 | 10/1987 | Bernardin | 604/378 |
| 4,888,238 | 12/1989 | Katz et al. | 604/375 X |

Primary Examiner—Michael Lusigman
Attorney, Agent, or Firm—Richard J. Gallagher; Thomas H. Whaley; William A. Aguele

[57] ABSTRACT

A fibrous web having an enhanced capacity for water absorption is produced by impregnating an absorbent fabric with a polymer or copolymer capable of forming by cross-linking an absorbent polymer or copolymer and subsequently heating the treated fabric effecting cross-linking of the polymer to form an absorbent polymer. The product may comprise a non-woven fibrous web or mat having a water-insoluble binder on one surface and a cross-linked hyrophilic polymer or copolymer on its opposite surface.

12 Claims, 2 Drawing Sheets

WATER ABSORBENT FIBER WEB

This is a division of application Ser. No. 07/225,294, filed 07/28/88, abandoned.

This invention relates to a fabric having an enhanced capacity for absorption of water. In one of its more specific aspects, this invention relates to a non-woven fabric comprising one or more webs of cellulose fibers associated with a hydrophilic polymer. The hydrophilic polymer is preferably applied to the cellulose fiber web as a liquid and cross-linked after application to the web. In a further specific embodiment of the invention a non-woven fibrous web of air laid fibers is treated on one side with a latex bonding agent and on the other side with a polymer capable of cross-linking or complexation to form an absorbent polymer. Non-woven fabrics encompassed by this invention are strong and durable and are useful in a number of applications, e.g. diapers, bed pads, etc. As used herein, the term polymer includes homopolymers and copolymers.

In another of its more specific aspects, this invention relates to a method for the production of water absorbent non-woven fabrics by spray application of a solution of a polymer onto an unbonded or partially bonded non-woven fibrous web and then effecting cross-linking or complexation of the polymer in situ to produce a superabsorbent polymer intimately bonded to the web.

It is the primary purpose of this invention to provide an improved non-woven web or fabric capable of absorbing and retaining considerable amounts of liquid. Such fabrics are useful for the production of absorbent pads, diapers, and similar end use items. To this end, a number of polymers and gums have been proposed as components of absorbent pads to provide enhanced water absorption capacity to webs and pads made of conventional fibers. For example, starchpolyacrylonitrile graft copolymers in finely divided form mixed with cellulosic fibers have been proposed in U.S. Pat. No. 4,055,184 as a filler in absorbent pads. Such materials are known in the art as "superabsorbents" due to their ability to absorb several times their own weight of liquid. In U.S. Pat. No. 4,500,315, the prior art relating to the use of superabsorbents in personal hygiene products is extensively discussed. As disclosed in this patent, the effectiveness of a superabsorbent is increased by laminating a web containing superabsorbent, an "absorbing layer", with a web acting as a wick, a "wicking layer". Superabsorbent particles are interspersed and fixed in the absorbing layer, e.g., by applying a liquid monomer to a fibrous web of synthetic staple fibers or nylon and subsequently polymerizing the liquid monomer to form a superabsorbent polymer.

The single web of our invention combines several functions of the multi-layer products. The bonding agent applied to one surface of the fibrous web is water pervious and may be used in an absorbent pad in contact with the skin without discomfort. That part of the web adjacent the bonding agent acts as a wick to distribute liquid over an area of the web larger than that initially wet by an aqueous liquid, e.g., by body fluid, and that part of the web remote from the bonded side acts as a superabsorbent. The web composition of this invention is relatively simple and inexpensive to manufacture as will be evident from the following detailed description.

The basic web may be multilayered and may comprise any of a number of non-woven fibrous webs, including but not limited to a carded web, an air-laid web, or a hydroentangled fibrous web, and may be made up of one or more kinds of fibers. A latex bonded, air-laid web comprising wood fibers, or a spunbonded or hydroentangled web, comprising wood pulp is preferred. The web may contain cotton, reconstituted cellulose fibers, polyester fibers, or meltblown polypropylene fibers in combination with wood pulp. Staple fibers may be blended with wood cellulose fibers or wood cellulose fibers may be spunlaced or hydroentangled with lightly bonded melt blown synthetic fibers.

Preferred superabsorbent polymers comprise carboxylated polymers which are crosslinked by metal ions or organic cross-linking agents when heated and dried on the base web. The superabsorbent polymer is formed when the substrate is dried, thereby effecting complexation or cross-linking of the polymers to form hydrophilic absorbent polymers.

Bonding agents commonly employed in the manufacture of paper towels and other non-woven fiber web products, including non-woven fabrics, synthetic leathers, and the like to impart strength and water repellency to the product, are suitable for use in the process and product of this invention. The bonding agents may be applied, e.g., by spraying an aqueous solution or dispersion of the bonding agent onto the web. Drying of the web results in curing of the bonding agent. Numerous bonding agents are known in the art including cationic starch; polyvinyl alcohol; pearl starch; natural gums (tragacanth, karaya, guar); natural latex; synthetic latex, including polyacrylates (e.g. polyethylacrylate, and copolymers); vinyl acetate-acrylic acid copolymers; polyvinyl acetates; polyvinyl chlorides; ethylene-vinyl acetates; styrenebutadiene carboxylates; polyacrylonitriles; and thermosetting cationic resins, (e.g., urea formaldehyde resins and polyamide-epichlorohydrin resins as disclosed in U.S. Pat. No. 3,819,470 incorporated herein by reference).

Suitable hydrophilic polymers for use in the method and products of this invention include one or more hydrophilic polymers of the following groups:

1) Polysaccharides: carboxyalkylcellulose, carboxylalkylguar; carboxyalkylhydroxyalkylguar; carboxyalkylhydroxyalkyl cellulose, wherein said alkyl groups are methyl, ethyl or propyl radical; karaya gum; xanthan gum; tragacanth gum; gum ghatti; carrageenin; psyllium; gum acacia; oxidized starches; oxidized cellulose; arabinogalactan; hemicelluloses; and ammonium or alkali metal salts thereof.

2) Homopolymers of acrylic or methacrylic acid and copolymers of acrylic or methacrylic acid with one or more ethylenically unsaturated comonomers and salts thereof; hydrolyzed and partially hydrolyzed polyacrylamides and salts; carboxylated polymers derived from homopolymerization of acrylonitrile or acrylamide and carboxylated polymers derived from copolymerization of acrylonitrile or acrylamide with one or more ethylenically unsaturated comonomers and salts thereof; and homopolymers or hydroxyethyl methacrylate, hydroxypropyl methacrylate and copolymers of hydroxyethyl methacrylate hydroxypropyl methacrylate, and salts thereof.

3) Carboxylated or partially carboxylated polymers derived from copolymerization of maleic anhydride and one or more ethylenically unsaturated comonomers, and esters, partial esters and salts thereof.

Suitable complexation agents include chelatable metallic salts and metallic complexes or partially alkylated metal compounds having a valence greater than one and a coordination number greater than two. This group includes zirconium, titanium, hafnium, iron, cobalt, aluminum, zinc and tin.

Organic cross-linking agents which are capable of cross-linking the appropriate hydrophilic polymer include di- and polyfunctional epoxides, aziridines, epihalohydrins, polyhaloalkanols, polyglycidyl ethers and amine-epihalohydrin adducts.

Specific examples of preferred methods of manufacture of webs containing polymeric hydrophilic absorbents in accordance with our invention are illustrated in the accompanying drawings.

Figure 2:
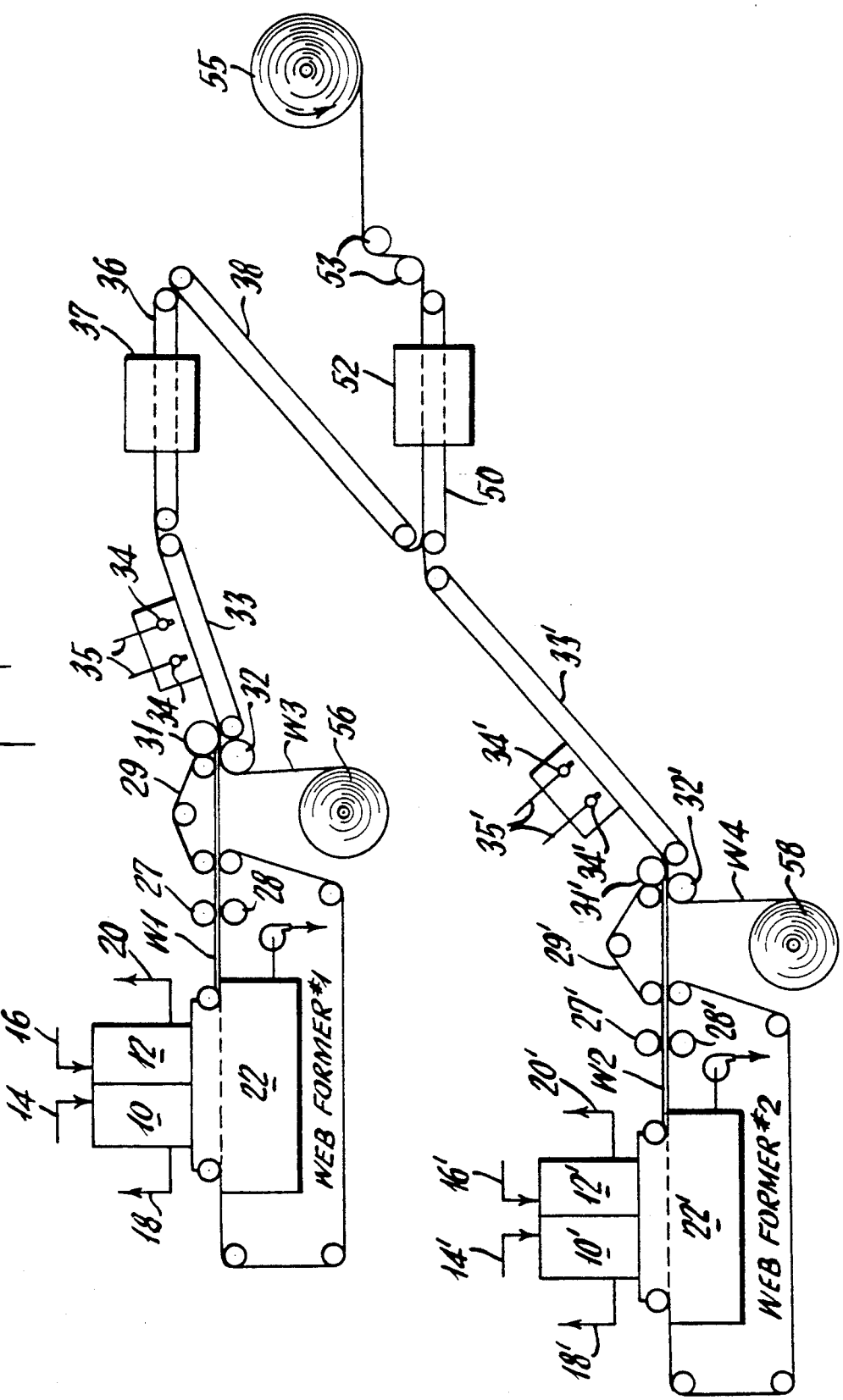

With reference to the drawings,

FIG. 1 illustrates diagrammatically an arrangement of apparatus suitable for producing a bonded web comprising a superabsorbent polymeric material, and FIG. 2 illustrates diagrammatically an arrangement of apparatus for producing a partially bonded, multiple layer web containing a superabsorbent material.

With reference to FIG. 1, an air laid web is formed in a Kroyer type machine as disclosed in U.S. Pat. Nos. 4,014,635 and 4,139,751, incorporated herein by reference. In such machines, the web-forming fiber is dispersed in a downwardly moving stream of air in a distributor housing, passed through a stationary screen, and directed onto a transversely moving forming-wire screen. Air is drawn through the forming-wire screen depositing the fibers on the forming wire as a web. In FIG. 1, the distributors include housings 10 and 12 provided with inlet conduits 14 and 16 for delivering fibers to the distributor housings in an air suspension. Fibrous material which is excessive in size, such as clumps or nits, is discharged from the distributor housings through return conduits 18 and 20 to a storage bin or hammermill as disclosed in U.S. Pat. No. 4,014,635.

Each of housings 10 and 12 is typically provided with finger-like impellers mounted on and rotated by a vertical shaft (not illustrated) as described in U.S. Pat. No. 4,193,751. The bottom of each housing is provided with a screen (not illustrated) and is open to a tunnel 22 from which air is exhausted by a fan 23.

The bottom, sides, and ends of the tunnel are closed except for openings at each end which are substantially sealed by rotatable sealing rolls 24 and 26. A moving forming-wire screen 25 travels from one end of the tunnel to the other, entering and leaving the tunnel through the openings provided with the sealing rolls.

Upon leaving the tunnel 22, the air laid web passes through heated compacting rolls 27 and 28, and is picked up by belt 29, passed through heated embossing rolls 31 and 32 onto wire 33 where it is sprayed with a suitable binder, e.g. a vinyl acetate latex by spray nozzles 34, supplied with binder through lines 35. The treated air laid web is transformed to belt 36 and passed through oven 37 where the latex binder is at least partially cured. From belt 36, the latex treated web is transferred to belt 38 and sprayed on its reverse side with polymeric superabsorbent precursors by spray nozzles 39 supplied through lines 40. From belt 38, the polymer wet web is carried through dryer 42 on belt 43 where the cross-linking or complexation of the precursors takes place forming the superabsorbent polymer in situ. Finally, the twice treated web is transferred to belt 44 and carried back under dryer 42 where the web is further dried and then passed to take up rolls 46 and wound onto reel 48 as product.

In the embodiment illustrated in FIG. 2, a first web of high bulk fibers, e.g. fluffed and dried hardwood pulp fibers, is produced in Web Former-1 as described in connection with FIG. 1 wherein like reference numerals designate like elements. A second web is similarly produced in Web Former-2 of conventional wood fibers, e.g. Southern softwood pulp fibers. The web from Web Former-1, designated "W1" is sprayed with a bonding agent, e.g. a polyvinyl acetate latex, by spraying on one side through spray nozzles 34 and cured in dryer 37. The web from Web Former-2, designated "W2" is sprayed with a suitable solution or dispersion of a polymer, e.g. a partially neutralized aqueous solution of polyacrylic acid containing a cross-linking agent, applied by spray nozzles 39'. The webs are combined into a two layer composite by laying the untreated side of web W1 on the treated side of web W2 on belt 50 of dryer 52. The layered web is passed through dryer 52 where the superabsorbent precursors are converted into a hydrophilic polymer or copolymer capable of imbibing relatively large amounts of water. The composite web is transferred to take up rolls 53 and wound onto reel 55 as product.

A separator web, e.g. a lightly bonded non-woven nylon web "W3" may be interlaid between webs W1 and W2 from a supply roll 56 if desired. The addition of separator web W3 provides added tensile strength to the product. Similarly, a web "W4", which may be a non-woven or loosely woven fabric, optionally a water impervious sheet, may be applied from supply roll 58 and integrated with the resulting composite web before it enters the dryer 52, as illustrated, or after leaving the dryer (not illustrated).

The following specific examples demonstrate the water absorption capabilities of webs produced by the method of our invention.

EXAMPLE 1

A two layer air-laid web having a basis weight of 55 pounds per 3,000 square foot ream is produced by air laying softwood pulp fiber marketed by Weyerhauser Corporation under the trade name Summit, and sprayed with a 12.5 weight percent aqueous solution of polyacrylic acid that contains 4 weight percent ammonium zirconium carbonate, based on the weight of the acrylic acid. The polyacrylic acid is marketed by Rohm and Haas Company, Philadelphia, Pa. under the trade name Acrysol-5. The ammonium zirconium carbonate is marketed by Magnesium Elektron, Flemington, N.J. In separate test runs, the pH of the polyacrylic acid solution was adjusted to 4.5 and to 5.5 by the addition of aqueous sodium hydroxide before addition of ammonium zirconium carbonate. In each case, the resulting solution was sprayed onto one side of an air-laid web through 0.015 inch orifice nozzles at 120 pounds per square inch pressure. Several tests were made at varying add-on rates reported as pounds polyacrylic acid per pound dry weight fiber.

The undried polymer treated web is covered with an air-laid web of fluffed and dried softwood sulfite pulp fibers marketed by Tembec Paper Company under the trade name Temfluff, and sprayed with a 17 weight percent vinyl acetate latex binder marketed by Air Products Company, Allentown, Penna. under the trade name A-109 at an ad on rate of 3.3 pounds latex solids per ream.

The resulting two ply composite web is heated in an oven to effect simultaneous curing of the latex polymer and the cross-linking of the polyacrylic acid with concomitant formation of the superabsorbent interpolymer of the partially neutralized polyacrylic acid.

Specimens of the product were tested for water holding capacity (WHC) by ASTM Standard Test Method for Water Holding Capacity of Bibulous Fibrous Products No. D 4250-83. In this method, specimens measuring 3 inches by 3 inches are cut from the product, weighed, partially immersed in water in a horizontal position for one minute, drained of excess water under carefully controlled conditions for 75 seconds and again weighed. The test is repeated on several samples and the results reported in grams of water held per square meter of the material under test. The water holding capacity is also reported as a water/fiber weight ratio.

Results of the tests are reported in Tables I and II.

TABLE I

Water Holding Capacity: One Minute
Initially Adjusted pH 4.5

| Specimen Number | PAA % Add-on | Water Holding Capacity | | |
|---|---|---|---|---|
| | | Gain (g) (Wet-Dry) | g. H$_2$O per sq. m. | Wt. Ratio (water/fiber) |
| 1 | 0 | 10.1 | 1727.8 | 31.0 |
| 2 | 1.3 | 9.3 | 1602.2 | 29.6 |
| 3 | 2.4 | 11.2 | 2006.4 | 35.4 |
| 4 | 3.7 | 10.0 | 1726.0 | 29.9 |
| 5 | 5.7 | 10.0 | 1726.1 | 29.5 |
| 6 | 7.8 | 9.2 | 1580.7 | 30.2 |
| 7 | 12.8 | 9.6 | 1646.1 | 26.7 |
| 8 | 17.9 | 9.0 | 1552.3 | 24.0 |
| 9 | 18.5 | 9.7 | 1674.4 | 28.7 |
| 10 | 37.7 | 11.1 | 1910.9 | 27.5 |

TABLE II

Water Holding Capacity: One Minute
Initially Adjusted pH 5.5

| Specimen Number | PAA % Add-on | Water Holding Capacity | | |
|---|---|---|---|---|
| | | Gain (g) (Wet-Dry) | g. H$_2$O per sq. m. | Wt. Ratio (water/fiber) |
| 11 | 3.0 | 11.5 | 1969.4 | 35.3 |
| 12 | 4.3 | 11.8 | 2024.5 | 33.2 |
| 13 | 6.6 | 11.8 | 2037.4 | 31.6 |
| 14 | 9.2 | 12.0 | 2061.4 | 33.8 |
| 15 | 11.7 | 10.4 | 1790.6 | 32.4 |
| 16 | 13.4 | 11.4 | 1953.1 | 34.0 |
| 17 | 20.8 | 11.1 | 1913.5 | 30.9 |
| 18 | 30.2 | 11.6 | 1989.2 | 31.8 |

EXAMPLE 2

The two layer air-laid web of Example 1 was tested for water retention by the method described in that example except that the specimens were partially immersed in water for five minutes before they were drained and weighed. Results of these tests are reported in Tables III and IV.

TABLE III

Water Holding Capacity: Five Minutes
Initially Adjusted pH 4.5

| Specimen Number | PAA % Add-on | Water Holding Capacity | | |
|---|---|---|---|---|
| | | Gain (g) (Wet-Dry) | g. H$_2$O per sq. m. | Wt. Ratio (water/fiber) |
| 19 | 0 | 9.8 | 1680.5 | 31.6 |
| 20 | 1.3 | 9.5 | 1635.8 | 32.3 |
| 21 | 2.4 | 12.5 | 2149.2 | 35.7 |
| 22 | 5.7 | 11.8 | 2037.3 | 34.9 |
| 23 | 5.7 | 11.8 | 2037.3 | 34.9 |
| 24 | 7.8 | 11.1 | 1906.6 | 35.2 |
| 25 | 12.8 | 12.7 | 2179.2 | 33.8 |
| 26 | 17.9 | 11.7 | 2009.0 | 34.9 |
| 27 | 18.5 | 12.5 | 2149.2 | 31.2 |
| 28 | 37.7 | 15.2 | 2621.3 | 33.6 |

TABLE IV

Water Holding Capacity: Five Minutes
Initially Adjusted pH 5.5

| Specimen Number | PAA % Add-on | Water Holding Capacity | | |
|---|---|---|---|---|
| | | Gain (g) (Wet-Dry) | g. H$_2$O per sq. m. | Wt. Ratio (water/fiber) |
| 29 | 3.0 | 13.0 | 2228.3 | 38.7 |
| 30 | 4.3 | 12.8 | 2194.7 | 36.5 |
| 31 | 6.6 | 13.3 | 2279.9 | 40.2 |
| 32 | 9.2 | 13.9 | 2387.4 | 38.1 |
| 33 | 11.7 | 13.4 | 2300.0 | 37.7 |
| 34 | 13.4 | 15.0 | 2578.3 | 44.2 |
| 35 | 20.8 | 12.8 | 2194.7 | 37.7 |
| 36 | 30.2 | 14.9 | 2546.5 | 41.5 |

We claim:

1. A method of manufacture of a non-woven superabsorbent fabric web which comprises forming an air laid web of cellulosic wood fibers, adding a latex bonding agent to one side of the air laid web and adding to the opposite side of the web at least one polymer precursor and cross-linking agent capable of forming an absorbent polymer upon heating, and then heating the resulting web for a period of time sufficient to cure the bonding agent and form the absorbent polymer.

2. A method of producing a superabsorbent fabric as defined in claim 1 wherein the polymer precursor is selected from the group consisting of oxidized starch, oxidized cellulose, aribinogalactan, hemicellulose, and ammonium or alkali metal salts thereof in aqueous solution.

3. A method of producing a superabsorbent fabric as defined in claim 1 wherein the polymer precursor is selected from the group consisting of hydroxyethyl methacrylate, hydroxypropyl methacrylate and copolymers thereof and salts thereof.

4. A method of producing a superabsorbent fabric as defined in claim 1 wherein the polymer precursor is a homopolymer of acrylonitrile or acrylamide.

5. A method according to claim 1 wherein the polymer precursor is a homopolymer of acrylic or methacrylic acid.

6. A method according to claim 1 wherein the polymer precursor is a copolymer of acrylic or methacrylic acid with at least one ethylenically unsaturated comonomer or salt thereof.

7. A method according to claim 1 wherein the polymer precursor is a hydrolyzed or partially hydrolyzed polyacrylamide or salt thereof.

8. A method according to claim 1 wherein the polymer precursor is a carboxylated polymer of acrylonitrile or acrylamide and an ethylenically unsaturated comonomer or salt thereof.

9. A method according to claim 1 wherein the polymer precursor is a homopolymer or copolymer of hydroxyethyl methacrylate or hydroxypropyl methacrylate or salt thereof.

10. A method of producing a superabsorbent fabric as defined in claim 1, wherein the cellulosic fiber web includes stable synthetic fibers.

11. A method of producing a superabsorbent fabric which comprises impregnating a nonwoven cellulosic fiber web with an aqueous solution of polyacrylic acid adjusted to a pH in the range of from about 4.5 to about 5.5 and about 4 weight percent ammonium zirconium carbonate based on the weight of the acrylic acid as cross-linking agent, and heating the impregnated fabric web for a period of time sufficient to form in situ a solidified hydrophilic polymer.

12. A method according to claim 11 wherein the ammonium zirconium carbonate is added to the aqueous solution of polyacrylic acid after the solution is adjusted to a pH in the range of from about 4.5 to about 5.5.

* * * * *